(12) United States Patent
Xu et al.

(10) Patent No.: US 9,989,496 B2
(45) Date of Patent: Jun. 5, 2018

(54) FIXED VALUE RESIDUAL STRESS TEST BLOCK AND MANUFACTURING AND PRESERVATION METHOD THEREOF

(71) Applicant: Beijing Institute of Technology, Beijing (CN)

(72) Inventors: Chunguang Xu, Beijing (CN); Lang Xu, Beijing (CN); Qinxue Pan, Beijing (CN); Dingguo Xiao, Beijing (CN); Xiao Li, Beijing (CN); Wentao Song, Beijing (CN)

(73) Assignee: BEIJING INSTITUTE OF TECHNOLOGY, Beijing (CN)

( * ) Notice: Subject to any disclaimer, the term of this patent is extended or adjusted under 35 U.S.C. 154(b) by 317 days.

(21) Appl. No.: 14/647,813

(22) PCT Filed: Mar. 12, 2013

(86) PCT No.: PCT/CN2013/072495
§ 371 (c)(1),
(2) Date: Sep. 28, 2015

(87) PCT Pub. No.: WO2014/082400
PCT Pub. Date: Jun. 5, 2014

(65) Prior Publication Data
US 2016/0033452 A1 Feb. 4, 2016

(30) Foreign Application Priority Data

Nov. 29, 2012 (CN) .......................... 2012 1 0498787
Nov. 29, 2012 (CN) .......................... 2012 1 0500267

(51) Int. Cl.
*G01N 29/04* (2006.01)
*G01N 1/28* (2006.01)
(Continued)

(52) U.S. Cl.
CPC .............. *G01N 29/04* (2013.01); *B23K 31/02* (2013.01); *B23K 31/125* (2013.01); *C21D 9/46* (2013.01);
(Continued)

(58) Field of Classification Search
CPC .......... G01N 29/04; G01N 1/28; B23K 31/02; B23K 31/125; B23K 15/006; B23K 15/06;
(Continued)

(56) References Cited

U.S. PATENT DOCUMENTS 4,348,131 A * 9/1982 Shimanuki ............... B23K 9/23
219/137 WM
5,557,048 A * 9/1996 Koike .................... G01N 29/07
73/597

(Continued)

FOREIGN PATENT DOCUMENTS

CN       1645091 A     7/2005
CN      101576450 A    11/2009

(Continued)

OTHER PUBLICATIONS

Japanese Patent Office Notification of Reasons for Refusal JP Patent Application No. 2015-544310; Applicant: Hirose, Takayuki et al., Date of Drafting: Heisei 28 Mar. 4, 2016, ( 2 pgs.)—Original in Japanese.

(Continued)

*Primary Examiner* — Helen Kwok
(74) *Attorney, Agent, or Firm* — Fish IP Law, LLP

(57) ABSTRACT

A fixed value residual stress test block, comprising a main body (1) and two welded blocks (2); the main body (1) and the welded blocks (2) are all rectangular metal blocks; the welded blocks (2) are welded onto the two opposite side surfaces of the main body (1); the main body (1) is deformed (Continued)

under the upper and lower pressures and generates residual stress. The fixed value residual stress test block has a simple structure.

11 Claims, 3 Drawing Sheets

(51) Int. Cl.
| | |
|---|---|
| *G01L 1/25* | (2006.01) |
| *G01N 3/00* | (2006.01) |
| *G01L 5/00* | (2006.01) |
| *B23K 31/02* | (2006.01) |
| *C21D 9/46* | (2006.01) |
| *B23K 31/12* | (2006.01) |
| *B23K 103/04* | (2006.01) |

(52) U.S. Cl.
CPC .............. *G01L 5/0047* (2013.01); *G01N 3/00* (2013.01); *B23K 2203/04* (2013.01); *G01N 2203/0296* (2013.01); *G01N 2203/0298* (2013.01); *G01N 2291/0421* (2013.01); *G01N 2291/0423* (2013.01); *G01N 2291/267* (2013.01)

(58) Field of Classification Search
CPC ........ B23K 15/0046; C21D 9/46; C21D 9/50; G01L 5/0047; G01L 1/25; G01L 1/241
See application file for complete search history.

(56) References Cited

U.S. PATENT DOCUMENTS

| | | | | |
|---|---|---|---|---|
| 6,032,851 A * | 3/2000 | Matherne | ............. | B23K 9/0286 219/61 |
| 6,290,905 B1 * | 9/2001 | Watanabe | .......... | B23K 35/3086 148/325 |
| 6,336,583 B1 * | 1/2002 | Wang | ..................... | B23K 31/02 228/175 |
| 7,690,553 B2 * | 4/2010 | Komlos | ................. | B23K 37/00 228/173.1 |
| 2001/0038001 A1 * | 11/2001 | Morikage | .......... | B23K 35/3086 219/137 WM |
| 2004/0250584 A1 * | 12/2004 | Offer | ........................ | B23P 9/04 72/56 |
| 2005/0242066 A1 * | 11/2005 | Statnikov | ............... | B23K 9/091 219/76.13 |
| 2006/0191878 A1 * | 8/2006 | Stol | ........................ | B23K 5/213 219/121.46 |
| 2007/0000328 A1 * | 1/2007 | Buttram | .................. | G01H 5/00 73/597 |
| 2007/0134059 A1 * | 6/2007 | Nakashima | ............. | B23K 9/02 403/271 |
| 2008/0123079 A1 * | 5/2008 | Numata | ................ | G01L 5/0047 356/35.5 |
| 2010/0006793 A1 * | 1/2010 | Takei | ................... | B23K 10/027 251/366 |
| 2011/0123820 A1 * | 5/2011 | Shimanuki | ............... | C21D 7/04 428/594 |
| 2012/0132290 A1 * | 5/2012 | Tonkovich | ........... | B01J 19/0093 137/14 |
| 2012/0237287 A1 * | 9/2012 | Honma | ................ | B23K 15/006 403/271 |
| 2012/0241420 A1 * | 9/2012 | Ishikawa | ............. | B23K 15/006 219/121.13 |
| 2012/0288324 A1 * | 11/2012 | Ishikawa | ............. | B23K 15/006 403/271 |

FOREIGN PATENT DOCUMENTS

| | | | |
|---|---|---|---|
| CN | 102053024 A | | 5/2011 |
| CN | 102519866 A | | 6/2012 |
| CN | 102706708 A | | 10/2012 |
| JP | 08240516 A | | 9/1996 |
| JP | 11200076 A | | 7/1999 |
| JP | 11-304677 | * | 11/1999 |
| KR | 10-2011-0109187 A | | 10/2011 |

OTHER PUBLICATIONS

Japanese Patent Office Notification of Reasons for Refusal JP Patent Application No. 2015-544310; Applicant: Hirose, Takayuki et al., Date of Drafting: Heisei 28 Mar. 4, 2016, ( 2 pgs.)—English Version.
State Intellectual Property Office of People's Republic of China, First Office Action issued for Chinese Application No. 20120498787.X, Applicant: Beijing Institute of Technology ( 8 pgs )—Original in Chinese.
State Intellectual Property Office of People's Republic of China, First Office Action issued for Chinese Application No. 20120498787.X, Applicant: Beijing Institute of Technology ( 8 pgs )—English Version.
State Intellectual Property Office of People's Republic of China, First Office Action issued for Chinese Application No. 201210500267.8, Applicant: Beijing Institute of Technology ( 8 pgs )—Original in Chinese.
State Intellectual Property Office of People's Republic of China, First Office Action issued for Chinese Application No. 201210500267.8, Applicant: Beijing Institute of Technology ( 9 pgs )—English Version.
ISA/CN, International Search Report, Int'l Appln No. PCT/CN2013/072495, dated Aug. 18, 2013 (5 pages).
Liu Peizhi; Study of Mechanism Using Two-Direction Pre-Stress to Control Welding Distortion and Hot Cracking; Dissertation for Master Degree in Engineering; China Academic Journal Electronic Publishing House, Jul. 2008; pp. 1-63.

* cited by examiner

FIXED VALUE RESIDUAL STRESS TEST BLOCK AND MANUFACTURING AND PRESERVATION METHOD THEREOF

BACKGROUND OF THE INVENTION

The present invention relates to a fixed value residual stress test block and manufacturing and preservation method thereof. The fixed value residual stress test block is adapted to correct an ultrasonic non-destructive testing system for residual stress.

DESCRIPTION OF THE RELATED ART

The non-destructive testing for residual stress is receiving much more attention, and the non-destructive testing method having vast potential of development at present is the residual stress testing with ultrasonic method. The ultrasonic method mainly tests residual stress by means of ultrasonic critical refraction longitudinal wave. The theory of ultrasonic stress testing has been very mature. However, the testing object of this method is relative value of residual stress, according to the theory. In order to test the absolute value of residual stress, it is necessary to develop a quantized standard test block for residual stress to correct a testing result and a testing system.

The current study relating to a standard test block for fixed residual stress aims mainly at a x-ray diffraction. In this case, the metal powder of material to be tested is cast as a test block of a certain size, and the residual stress is standardized on the basis of the lattice change of the cast test block. Moreover, the researchers of the UK bend steel material to bow shape, so that a residual stress test block is manufactured by bending. The structure of these test blocks is very special, resulting in that the manufacturing method is too complicated to be achieved. For this, it is hoped to get a fixed value residual stress standard test block of simple structure, which is accurate and reliable and obtained by a simple method.

SUMMARY OF THE INVENTION

The purpose of the invention is to provide a fixed value residual stress test block and manufacturing and preservation method for correcting an ultrasonic non-destructive test system for residual stress, so as to detect the absolute value of residual stress accurately and reliably.

The fixed value residual stress test block comprises a main body and two welded blocks. Both of the main body and the welded blocks are rectangular metal blocks. The welded blocks are welded to two opposite sides of the main body. The main body deforms due to bearing a pressure in up and down direction, and generates residual stress.

The fixed value residual stress test block according to the invention has a simple, accurate and reliable structure.

The invention further provides a manufacturing method for fixed value residual stress test block, which has the following manufacturing procedure: manufacturing main body of the test block and two welded blocks; applying a pressure to the main body of the test block in up and down direction so as to deform the main body to generate residual stress; welding the two welded blocks to two opposite sides of the main body; canceling the pressure applied in up and down direction.

The aforementioned method is very simple. The fixed value residual stress test block manufactured by the method is accurate and reliable.

The invention further provides a preservation method for fixed value residual stress test block. The test block is stored in an environment with constant-temperature of which the range is 2~8° C., and is kept away from impact and vibration.

The preservation method can make the residual stress test block maintain stable residual stress.

Symbols: 1. main body, 2. welded block, 3. weld seam, 4. upper pressure-head of compression-testing machine, 5. lower pressure-head of compression-testing machine, 6. measurement area.

DETAILED DESCRIPTION OF THE INVENTION

According to the invention, the fixed value residual stress test block is manufactured by weld. According to the invention, two welded blocks are generally welded on symmetric positions of a pressed main body. The tensile stress is generated to the welded blocks by rebound effect of the main body. The different deformation corresponds to the different stress. The test block having desirable stress can be obtained by controlling the deformation of the test block via calculation based on the theory.

The embodiment of the invention will be described in detail with reference to the drawings.

Figure 1:
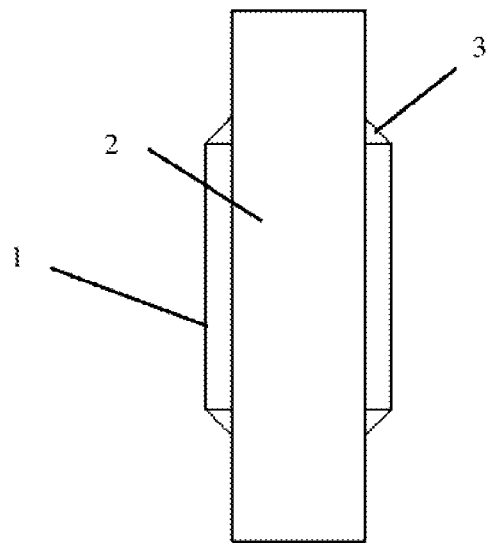
FIG. 1 shows the side view of the fixed value residual stress test block.

Take steel 45 for example, as FIG. 1 shown, the size of the main body 1 is 30 mm×30 mm×130 mm. The size of the welded blocks 2 is 30 mm×5 mm×70 mm.

Two welded blocks 2 are welded to both sides of the main body 1 of the fixed value residual stress test body. The welded blocks 2 are arranged at central position of the main body 1. In a case that the main body 1 is pressed by a compression-testing machine, the welded blocks 2 are welded to the main body 1. The rebound effect of the main body 1 generates a certain residual stress between the welded blocks 2 and the main body 1. The residual stress value of the test block can be known on the basis of the deformation of the main body 1 and the welded blocks 2. The different deformation corresponds to the different stress.

The unidirectional pressure stress is generated by pressing the main body 1 of the test block within limit of elasticity. The main body 1 will rebound after pressure being canceled. The welded blocks 2 and the main body 1 before rebounding are welded together by welding technique, so as to restrict and interact with each other. Then, the tensile stress or pressure stress is generated between the welded blocks 2 and the main body 1. According to this theory, the fixed value residual stress test block can be manufactured by pressing and welding and controlling the deformation of the main body 1 and the welded blocks 2. The weld seam 3 is entirely continuous.

In the process of manufacturing the test block, the key point is the accurate control for the deformation of the main body 1 and the welded blocks 2. The accurate control for residual stress of the test block is based on the accurate control for the deformation. However, the preservation technique is also very important during the test block being used.

The manufacture of the fixed value residual stress test block is as follows:

Take steel 45 as manufacture material of the test block for example, as FIG. 1 shown, it is formed to be two parts of the test block. The size of the main body 1 is 30 mm×30 mm×130 mm. The size of the welded blocks 2 is 30 mm×5 mm×70 mm. The surface roughness of the main body 1 and the welded blocks 2 is less than or equal to Ra6.4.

The main body 1 and the welded blocks are tempered, so as to eliminate process stress of the test block and make the test block be in a stress-free state.

According to the Hooke's law, the applied pressure, i.e. load applied by the compression-testing machine to end surface of the main body 1 is calculated, on the basis of the cross-sectional area of the main body 1 and the welded blocks 2 and required stress value of the test block.

Figure 2:
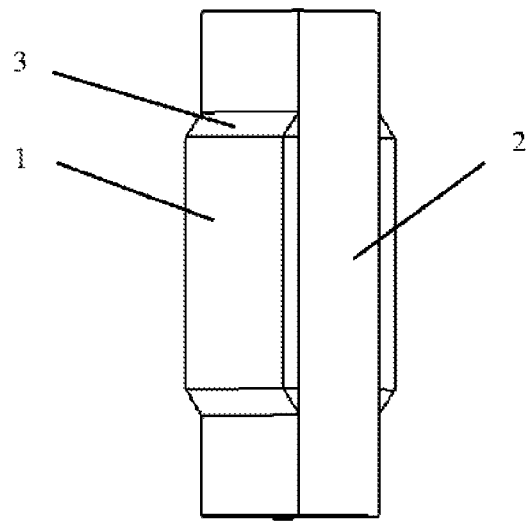
FIG. 2 shows the front oblique view of the fixed value residual stress test block.
Figure 4:
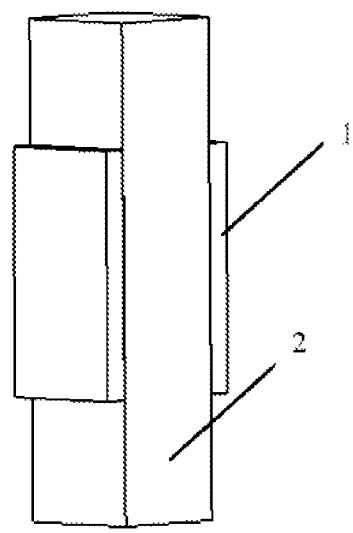
FIG. 4 shows the front oblique view of locating position of each parts of the fixed value residual stress test block.

As FIG. 2 and FIG. 4 shown, the two welded blocks 2 and the main body 1 are closely attached together by bounding.

Figure 5:
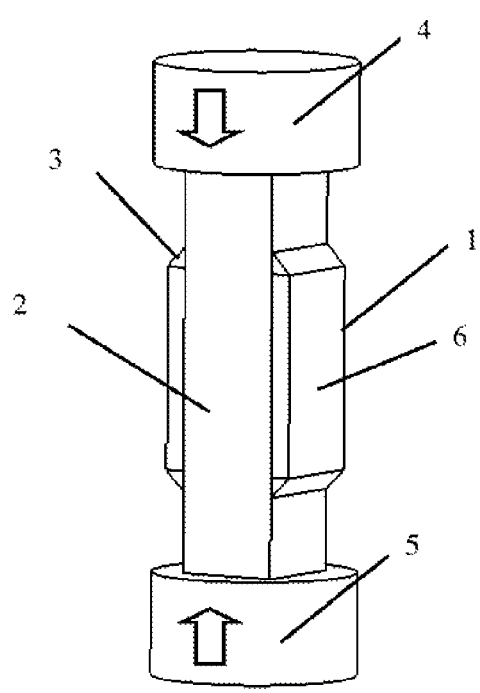
FIG. 5 shows the welding process of the fixed value residual stress test block.

As FIG. 5 shown, the main body 1 is put between the upper pressure-head 4 and lower pressure-head 5 of the compression-testing machine. The compression-testing machine is set based on predetermined (calculated) load to press the main body 1. The hollow arrows in the figure show the pressed directions. The 30 mm×30 mm surfaces of the main body 1 are pressed surface. After a calculation load being achieved, the load is maintained stable for a while, and then the welded blocks 2 are welded to the main body 1 in a case that the load is not unloaded. It is ensured as far as possible that the main body 1 and the welded blocks 2 do no have obvious deformation during welding. The contacted edges of the contacted surface between the main body 1 and the welded blocks 2 should be entirely covered by weld seam.

After the welding for welded blocks 2 being completed, an air cooling is applied to the test block in a case that the load is not unloaded. After the test block being cooled, the compression-testing machine is removed, and the manufacture for the test block is completed. After then, the stress of the fixed value test block is measured and recorded, and is compared to a theoretical value.

If the welded test block having different residual stress is required, it only needs to apply different pressure to the main body 1, and then perform an operation according to aforementioned steps.

Figure 3:
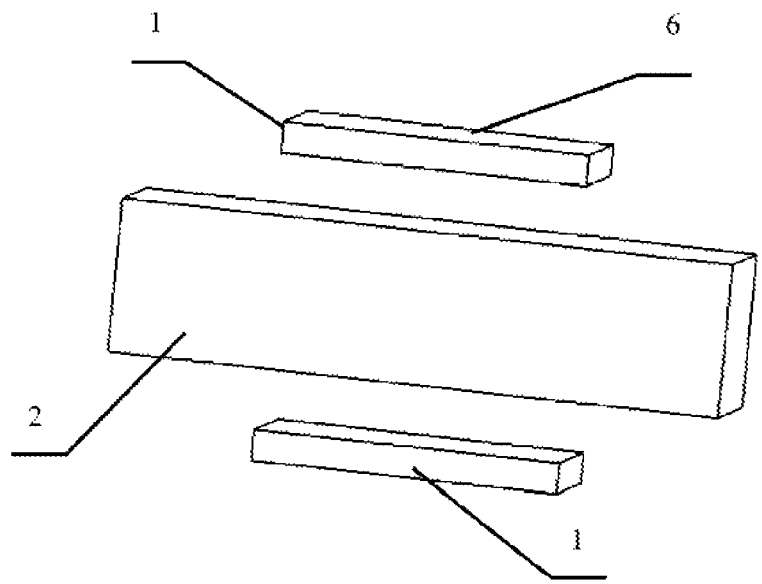
FIG. 3 shows the exploded view of position relationship between each parts of the fixed value residual stress test block.

During correction of an ultrasonic non-destructive test system for residual stress using the fixed value residual stress test block, a detection sensor is paced on the welded blocks 2 along the pressed direction of the main body 1, so as to couple the detection sensor to the test block well. After being stable, it starts to detect and correct the test block. As FIGS. 3 and 5 shown, the fixed value measurement areas 6 of the fixed value residual stress test block are on the outer side surfaces of the two welded blocks 2, and these two measurement areas 6 are only suitable to a detection method of ultrasonic critical refraction longitudinal wave and a detection method of surface wave.

Currently, there are methods for eliminating residual stress in domestic and overseas, such as tempering, vibratory stress relief, ultrasonic wave impact, and natural stress relief. These methods achieves that local organization of the welded piece is reorganized under the action of alternative change of temperature and alternative load, such as vibration and impact, so that the residual stress is released. The stable constant temperature may reduce the thermal expansion and reorganization of the test block, so that the residual stress may be maintained for a long time.

For this, in order to make the fixed value residual stress test block maintain a stable residual stress, the test block should be stored in constant temperature environment, such as calorstat, where the temperature is 2° C.~8° C., after the fixed value residual stress test block being manufactured and the residual stress being measured, so as to eliminate the thermal expansion of the test block caused by alternative change of temperature, and to avoid the residual stress is continuously loosed. Furthermore, the impact and vibration which may cause the residual stress release should be avoided, during storing the test block. The change of the residual stress of test block is regularly monitored and recorded during storing the test block. The test block should be put back into the calorstat in time after correcting the ultrasonic detection system for residual stress at each time.

The invention claimed is:

1. A fixed value residual stress test block comprising a main body and two welded blocks, both of said main body and said welded blocks are rectangular metal blocks, said welded blocks are welded onto two opposite side surfaces of said main body while said main body is deformed under pressures in up and down directions such that, when the pressures on the main body in the up and down directions is removed, a rebound effect of the main body generates a residual stress between the main body and welded blocks.

2. The fixed value residual stress test block according to claim 1, wherein, width of said welded blocks is the same width of said side surfaces on which said welded blocks are welded, length of said welded block is less than length of said main body, said welded blocks are welded on central positions of said side surfaces of said main body, said central positions are symmetric.

3. The fixed value residual stress test block according to claim 1, wherein, contacted edges of a contacted surface between the main body and the welded blocks are entirely covered by weld seam.

4. The fixed value residual stress test block according to claim 1, wherein, material of said main body and said welded blocks are at least one of steel 45, steel Q235 and steel Q345.

5. The fixed value residual stress test block according to claim 1, wherein, a surface roughness of said main body and said welded blocks is less than or equal to Ra6.4.

6. The fixed value residual stress test block according to claim 1, wherein, said residual stress is calculated according to deformation amount of said main body and said welded blocks with the Hooke's law.

7. The fixed value residual stress test block according to claim 1, wherein, the fixed value measurement areas of said fixed value residual stress test block are on outer side surfaces of the two welded blocks, and the fixed value measurement areas are only suitable to a detection method of ultrasonic critical refraction longitudinal wave and a detection method of surface wave.

8. A manufacturing method for fixed value residual stress test block, comprising:
  manufacturing a main body and two welded blocks of said test block, wherein both of said main body and said welded blocks are rectangular metal blocks;
  applying pressure in up and down direction to said main body of said test block, so that said main body is deformed;

welding said welded blocks onto two opposite side surfaces of said main body; and canceling pressure applied in up and down direction such that a rebound effect of the main body generates a residual stress between the main body and the welded blocks.

9. The manufacturing method according to claim 8, wherein, in a process of manufacturing said main body and said two welded blocks of said test block, tempering said main body and said welded blocks after said process being completed, so as to eliminate stress of said test block generated in the process.

10. The manufacturing method according to claim 8, wherein, before welding said main body and said welded blocks, smoothing adjacent surfaces of said main body and said welded blocks, after then attaching said main body and said welded blocks together closely.

11. The manufacturing method according to claim 8, wherein, after welding for said welded blocks being completed, cooling said test block by the air before canceling the pressure applied in up and down direction.

\* \* \* \* \*